United States Patent [19]

Donohue

[11] 4,381,229

[45] Apr. 26, 1983

[54] PROCESS FOR ELECTROCHEMICAL REDUCTION OF TEREPHTHALIC ACID

[75] Inventor: John A. Donohue, Elmhurst, Ill.

[73] Assignee: Standard Oil Company (Indiana), Chicago, Ill.

[21] Appl. No.: 319,120

[22] Filed: Nov. 9, 1981

Related U.S. Application Data

[63] Continuation-in-part of Ser. No. 201,139, Oct. 27, 1980, abandoned.

[51] Int. Cl.³ .............................................. C25B 3/00
[52] U.S. Cl. .................................... 204/75; 204/73 R
[58] Field of Search ............................... 204/75, 73 R

[56] References Cited

U.S. PATENT DOCUMENTS 3,929,613 12/1975 Michelet ............................... 204/77
3,984,294 10/1976 Nohe et al. ........................... 204/75

FOREIGN PATENT DOCUMENTS 2510920 9/1976 Fed. Rep. of Germany ........ 204/75
2642496 3/1978 Fed. Rep. of Germany ........ 204/75

Primary Examiner—John F. Niebling
Attorney, Agent, or Firm—William C. Clarke; William T. McClain; William H. Magidson

[57] ABSTRACT

Terephthalic acid is electrochemically reduced to p-hydroxymethylbenzoic acid in a process in an electrolysis cell in which (a) the cathode is solid and metal with an amalgam of mercury surface and has a hydrogen overvoltage which is greater than the potential for the reduction of terephthalic acid to p-hydroxymethylbenzoic acid, and, (b) sufficient mercury is added of a mercury compound to maintain the process.

23 Claims, No Drawings

PROCESS FOR ELECTROCHEMICAL REDUCTION OF TEREPHTHALIC ACID

CROSS REFERENCE TO RELATED APPLICATIONS

This application is a continuation-in-part of U.S. Ser. No. 201,139 filed Oct. 27, 1980, now abandoned.

BACKGROUND OF THE INVENTION

This invention relates to a process for the electrochemical reduction of terephthalic acid to p-hydroxymethylbenzoic acid (pHMBA) and more particularly to improvements in the electrical efficiency of the said reaction and to operation by treatment of the cathode to obtain a mercury overlay as an amalgam on the cathode surface and the addition of a soluble salt of mercury, which regenerates the amalgam overlay, to the electrolysis catholyte solvent.

Inasmuch as the cost of electric power utilization in the electrochemical conversion of terephthalic acid to p-hydroxymethylbenzoic acid has a direct bearing on the economics of this process it is highly desirable to increase current efficiency and to hold side reactions which do not lead to the desired product to a minimum. If only one series of reactions were taking place in the instant process, that is, the electrochemical reduction of terephthalic acid to p-hydroxymethylbenzoic acid at the cathode, the ideal of 100% conversion of the starting material to the desired product would be achieved. However, as in the case with most electrochemical reactions, this particular reaction is not so simple and many competing reactions can take place in the electrolysis cell. The resulting presence of 4-carboxybenzaldehyde (4-CBA), dihydroxymethylbenzene, toluic acid and other impurities render resulting p-hydroxymethylbenzoic acid undesirable for use as a monomer for polymer applications without further expensive purification.

It is well-known that in the cathodic reduction of carboxylic acids that two types of products can result, either the corresponding aldehyde in a two-electron process or the hydroxymethyl compound in a four-electron process wherein the aldehyde is further reduced to the alcohol. (M. Baizer, *Organic Electrochemistry*, Dekker, N.Y., (1973), 414). The alcohol can be further reduced to the methyl group.

A further complication in the electrolysis of terephthalic acid to p-hydroxymethylbenzoic acid is the development, as the electrolysis proceeds, of a deactivating or poisoning layer which accumulates on the cathode if a solid cathode such as lead is used. Current efficiency accordingly suffers. Continuous mercury cathode cells have been developed for the electrolytic reduction of phthalic acid to overcome this same problem (P. C. Condit, *IEC*, 48, 1252 (1956)). However, use of solid cathodes versus the use of liquid cathodes has the advantage of simplicity in construction and versatility.

In the prior art, it is known that the reduction of aromatic carboxylic acids at lead or mercury cathodes in a protic solvent (proton-donor) i.e., alcoholic, etc., gives excellent yields of corresponding benzyl alcohols (*Chem. Ber.*, 38, 1747 (1905); ibid, 39, 2933 (1906); *Ann.*, 417, 69 (1929); *Org. Syn.* 21, 10 (1941)). Baizer (op. cit. 417) suggests that the mechanism of this process in strongly acidic alcoholic media may be that the carboxylic acid is reduced in its protonated form, $RCOOH_2^+$, or that the acid first forms an ester with the alcoholic solvent, the ester being more reducible than the acid. Ono, *Nippon Kagaku Zasshi*, 75, 1195-9 (1954) (CA51:12704b) teaches the electrolytic reduction of phthalic and isophthalic acid and their esters using a mercury cathode gave two types of reactions, reduction of the side chain and the benzene ring, phthalic acid giving dihydrophthalic acid and dimethyl isophthalate giving m-hydroxymethylbenzoic acid. Ono, et al., *J. Chem. Soc., Japan*, Pure Chem. Section, 74, 907–11 (1953) (CA48:8082d) reported electrolytic reduction of dimethyl terephthalate to p-methylhydroxymethylbenzoate using a mercury cathode. German Offenlegungsschrift No. 24 28 878 teaches a process for production of p-hydroxymethylbenzoic acid esters by electrochemical reduction of dimethylterephthalate on solid electrode cathodes (lead, zinc, cadmium, graphite and amalgamated metals—lead, copper, etc.) with methanol as solvent. However, the poisoning effect has plagued the application of electrolytic reduction processes to aromatic carboxylic acids. Natarajan, et al., *Electrochem. Technol.*, 2 (5-6), 151-6 (1964) (CA61:6940c) reports in the electrolytic reduction of benzoic acid to benzyl alcohol using a rotating lead cathode, the reaction proceeds with good current efficiency until the electrolyte is saturated with benzyl alcohol, at which point the cathode becomes covered with a layer of benzyl alcohol, effectively hindering the diffusion of benzyl alcohol with resultant decrease in current efficiency. German Offenlegungsschrift No. 26 42 496 teaches a process for the production of p-hydroxymethylbenzoic acid by the electrochemical reduction of terephthalic acid in the presence of ammonia (a basic protic solvent) using electrodes such as mercury, lead, cadmium and antimony. Lead is indicated as especially suitable. Unfortunately, activity drops off rapidly after a few minutes. The problem of maintaining cathode activity is met by discontinuing the direct current periodically and shorting out the cell for periods of ½ to 3 minutes. From the physical constants given in this publication for the p-hydroxymethylbenzoic acid (melting point of 182.5° to 183.5° C.; conversion 100% and selectivity 91%) it is probable that the electrochemical product of terephthalic acid is not a pure product but contains 4-carboxybenzaldehyde or toluic acid. The large excess of current taught as used, 15.3 Faradays, 4.0 Faradays being 100% of theoretical, indicates the difficulty of maintaining cathode activity of a lead cathode.

Accordingly, it is an object of the present invention to develop an electrochemical process for the manufacture of p-hydroxymethylbenzoic acid from terephthalic acid which avoids the above disadvantages. It is an object of the present invention to provide a process for production of p-hydroxymethylbenzoic acid wherein the production of by-product impurities, namely, 4-carboxybenzaldehyde, dihydroxymethylbenzene and toluic acid is minimized. It is a further object of this invention to increase the current efficiency of the electrochemical reduction process over that of previously known methods for electrochemical reduction of terephthalic acid to p-hydroxymethylbenzoic acid. It is another object of this invention to provide an efficient continuous process for the electrochemical production of p-hydroxymethylbenzoic acid wherein discontinuance of the reductive process is not required by the development of a poisoning barrier upon the cathode. Other objects will appear hereinafter.

SUMMARY OF THE INVENTION

Terephthalic acid is electrochemically reduced to p-hydroxymethylbenzoic acid in a process in an electrolysis cell in which (a) the cathode is solid and metal with a mercury overlay as an amalgam surface and has a hydrogen overvoltage which is greater than the potential for the reduction of terephthalic acid to p-hydroxymethylbenzoic acid, and (b) sufficient mercury is added as a mercury compound to maintain the process. Addition of a mercury compound is essential. For example, current efficiency decreases in continuous operation and cathode amalgam surfaces lose amalgamation without addition of a mercury compound.

DETAILS OF THE INVENTION

The term "current efficiency" is defined as ratio of consumption in Faradays used to make product to total Faradays used times 100. The term "amalgam" is defined as referring only to an alloy of mercury.

The present invention provides a process for the electrochemical preparation of p-hydroxymethylbenzoic acid with improved current efficiency and minimal production of by-product impurities. The process comprises performing the cathodic reduction in an electrolysis cell having a cathode compartment and an anode compartment. The anode and cathode compartments can be separated by a cation exchange diaphragm, although the presence of a separating diaphragm is not an essential element of the invention. If a separating diaphragm is used, the cathode and anode and the separating diaphragm are preferably in parallel planes. Advantageously, several of the elementary electrolysis cells can be combined in the manner of a filter press.

In general, any metal with a higher hydrogen overvoltage than the potential for the reduction of terephthalic acid to p-hydroxymethylbenzoic acid which will form an alloy with lead and an amalgam with mercury is suitable. Examples of material forming the cathode are lead and alloys of lead with cadmium, antimony, tin or bismuth. The cathode is prepared by abraiding in a suitable manner the surface of the solid cathode to remove any metal oxidation and then contacting the abraided metallic surface with mercury to form the amalgam. In the case of lead, it is sufficient to abraid the surface of the lead solid to remove all forms of lead oxide and any other impurities. Liquid mercury of 99.9% purity is used as a bath for the abraided solid lead cathode. In the case of lead, the lead amalgam is formed in the surface of the lead at room temperature upon contacting the mercury bath.

The anode of the electrolysis cell usually consists of a solid electrically conducting material which is electrochemically stable in the anolyte and under the operating conditions considered. Examples of such materials are metals and metalloids such as platinum, platinised titanium, graphite, lead and its alloys, particularly with silver, antimony or tin.

Optionally, any known cation exchange membrane can be used to separate the catholyte from the anolyte, but membranes of the homogeneous type are preferred. These membranes optionally can be reinforced with a screen. For carrying out electrolysis operations over a long period, it is naturally preferred to use membranes which do not swell and which are stable to the action of the various constituents of the catholyte and the anolyte. Examples of such membranes are those of Nafion (trademark of E. I. DuPont de Nemours & Co.) perfluorosulfonic acid.

The catholyte can comprise a neutral solvent, a weakly basic solvent or an aprotic solvent i.e., acetonitrile, to which a source of protons has been added. Examples of neutral solvents are water, methanol and other alcohols mixed with water to obtain necessary solvent properties. Examples of basic solvents are ammonia, methylamine, ethylenediamine which are diluted suitably to maintain a weak basic condition. In a suitable method of operation, the catholyte consists of a solvent, preferably water, and terephthalic acid with a soluble ammonium salt and ammonia. At the start of electrolysis, the catholyte contains sufficient ammonia to form a diammonium salt of terephthalic acid. Less ammonium salt is required as the electrolysis process proceeds. Concentration of ammonia as ammonium hydroxide is within the range of from about 1 gram of ammonium hydroxide per 2 grams of terephthalic acid to about 1 gram of ammonium hydroxide per gram of terephthalic acid and wherein the pH of the resulting solution is at least 6.5, preferably with a pH within the range of from about 8.5 to about 9.5. The concentrations of terephthalic acid and ammonium salt can be either constant when the reaction is carried out continuously, or variable when the reaction is carried out discontinuously. In all cases, the concentration of terephthalic acid is less than the saturation concentration at the temperature of electrolysis; generally, this concentration is greater than 2% by weight, and preferably greater than 3% when the current density is high, these values relating particularly to the constant concentration when the reaction is carried out continuously and to the final concentration when the reaction is carried out discontinuously. The concentration of ammonium salt is usually between about 0.1% to about 10% by weight, and preferably between about 0.1% to about 1.0% by weight, these values relating particularly to the total solution of water, terephthalic acid and other solution components when the reaction is carried out continuously and to the final solution when the reaction is carried out discontinuously. The ammonium salt can be any ammonium salt but a salt selected from the group consisting of ammonium chloride, ammonium sulfate and ammonium carbonate is preferred.

The catholyte can also contain reaction by-products in small amounts, generally less than 1% by weight.

An aqueous acid solution is preferably used as the anolyte, though any other anolyte capable of providing electrical conductivity between the two electrodes can be used. Aqueous solutions of sulphuric or phosphoric acids are usually employed in a concentration generally of 0.1 to 5 mols/liter, and preferably 0.5 to 2 mols/liter.

The current density at the cathode is within the range of from about 1 to about 200 amperes per decimeter squared ($A/dm^2$), preferably from about 20 to about 100 $A/dm^2$.

The flow of the catholyte in a closed circuit is usually achieved by means of a pump. The circuit can in addition contain attached devices such as a heat exchanger or an expansion vessel. The expansion vessel enables terephthalic acid to be added to the catholyte and also some catholyte to be withdrawn in order to extract the p-hydroxymethylbenzoic acid. By-product hydrogen is also removed.

The anolyte can also be circulated, preferably in an anolyte circuit similar to that of the catholyte, so that the pressure on either side of the separating diaphragm can be substantially the same.

At least one spacer is preferably present in the anode and cathode compartment if a cation exchange membrane is used. These spacers serve to prevent deformations of the cation exchange membrane and prevent contact between this membrane and the electrodes. These spacers also help to render uniform the spacing between the membrane and electrodes which contains the electrolyte. These spacers are generally manufactured from synthetic polymers which are chemically inert and which do not conduct electricity; they can be made in the form of interlaced, intertwined, knotted or welded yarns (e.g., woven fabrics, grids or nets) or they can be in the form of plates possessing holes or grooves. In practice, these spacers are oriented along planes which are parallel to those of the electrodes and the separating diaphragm.

Terephthalic acid reduction can be monitored to obtain 100% conversion. Less than 100% conversion is preferable. Less than 96% conversion is more preferable. Undesirable by-products are produced at high conversion levels. Increased amounts of impurities such as dihydroxymethylbenzene and toluic acid can result at terephthalic acid conversion levels of greater than 95–96%. Percent conversion is preferably balanced to obtain maximum conversion to p-hydroxymethylbenzoic acid and minimum conversion to undesirable by-products.

Terephthalic acid, under ambient conditions being virtually insoluble in water, requires a weak base as a reactant to form a soluble salt in water. Examples of suitable weak bases are ammonia, methylamine and ethylenediamine but any similar weak base can be used.

In the practice of the invented electrolysis process a weak base such as ammonia and a salt such as an ammonium salt are added initially to the catholyte, the ammonia in a concentration sufficient to dissolve the terephthalate acid in the solvent, i.e., water, liquid ammonia, etc. but which is preferably water, and a ammonium salt to carry the current. After an initial period of operation, a monoammonium salt of terephthalic acid is added to maintain a basic condition sufficient to cause additions of terephthalic acid to dissolve, with pH above 6.5 and preferably with a pH within the range of about 8.5 to about 9.5, to insure complete solubility of the terephthalic acid. Concurrently with the addition of the monoammonium salt of terephthalic acid, a mercury compound, preferably a solvent-soluble mercury salt, is added to the catholyte in an amount sufficient to maintain the continuous process, to provide a minimum concentration of mercury metal ion of from about 5 to 1000 parts per million (ppm) expressed as the metal. Concentrations of mercury metal ions greater than 1000 ppm can be used if suitable. Examples of mercury salts soluble in aqueous solutions are mercuric acetate, mercuric bromide, mercuric chlorate, mercuric chloride, mercuric cyanide. Mercuric acetate is preferred because of high solubility and easy availability.

At the end of electrolysis, the p-hydroxymethylbenzoic acid is isolated from the electrolyte by known means, which optionally can be by the difference in water solubility between that of terephthalic acid and p-hydroxymethylbenzoic acid. Using this method, the catholyte is acidified and filtered hot, within a temperature range of from about 75° C. to about 100° C., to remove terephthalic acid. The p-hydroxymethylbenzoic acid is obtained by cooling the mother liquor, optionally after concentrating under reduced pressure. The cooling is carried out at temperatures below 40° C. and preferably below 25° C., the degree of concentration and the cooling temperature naturally vary according to the degree of purity desired for the p-hydroxymethylbenzoic acid.

The process of the invention possesses numerous advantages in addition to the advantages of continuous operation; it makes it possible to use catholyte solutions which facilitate workup and recovery of the p-hydroxymethylbenzoic acid; it allows electrolysis cells to be produced which are compact and easy to dismantle; it allows gases to be removed easily which are produced at the anode, especially oxygen, and are capable of causing high resistance between the electrodes due to gas bubbles; it makes it possible to use high current densities and to achieve easily the supply of electricity in series between the various elementary electrolysis cells in an assembly of several cells; it makes it possible to use cells with vertical electrodes. Finally, due to the constant geometrical shape of the preferred electrolysis cells, the anolyte and the catholyte can be circulated very rapidly, enabling lower concentrations of terephthalic acid to be employed and, as a result, better degrees of conversion can be obtained in continuous operation.

The following examples illustrate the invention. The chemical yields indicated are yields of p-hydroxymethylbenzoic acid relative to initial quantities of terephthalic acid present. Concentrations of solutions are expressed as the number of grams of solute per liter of solution.

EXAMPLE I

Batch reduction of terephthalic acid to p-hydroxymethylbenzoic acid was carried out in an electrolysis cell in the following manner. The cell was mounted in an oil bath which was used to heat the electrolyte to reaction temperature before starting and to cool the electrolyte once the reaction had started. The oil bath was fitted with an electric heater, a source of cooling comprising coils filled with cooling water and a mechanical stirring means. The cell was a 600 ml glass beaker fitted with a stopper of fluorocarbon rubber. Holes through the stopper gave entrance to a thermometer, the anode leads and the cathode leads. The anode support was a glass anolyte tube which was fitted with a fluorocarbon plastic holder to support the anode and a semi-permeable membrane. The anode was a circular platinum screen about 2.5 cm in diameter. The membrane was of sulfonated fluorocarbon polymer. The glass tube served as the anolyte chamber. The fluorocarbon plastic holder was inclined at an angle from the horizontal to permit gases rising from the cathode to escape. The cathode was a metal disc about 6 cm in diameter. The cathode was of electrolytically pure lead of 99.9% purity. A magnetic stirring bar was placed on top of the cathode disc in the bottom of the glass beaker which served as the electrolysis cell.

In operation, the catholyte solution was placed in the cell with the cathode and with the stirring bar in place. The anode was inserted in the anolyte chamber, the chamber was filled with anolyte and inserted in the fluorocarbon stopper. The anolyte chamber was thereupon checked for membrane leakage and placed on the cell. The thermometers were inserted in the fluorocarbon stopper and the cell was assembled. Heat can be applied to the completed cell by means of an oil bath to reach the necessary temperature at which time the heat application is stopped. The cooling system is thereupon activated and as soon as the cell temperature began to drop, the electrolysis reaction is started by applying a source of direct current. Alternatively, the reaction could be started at room temperature and reach operating temperature without direct heating. Alternatively, the cell could be operated without the presence of a semipermeable membrane.

Current density was controlled so as to maintain consumption of electricity slightly below the calculated quantity of 4 Faradays required for one equivalent weight of terephthalic acid.

An aqueous solution of 2% sulfuric acid, approximately 0.2 mols/liter of water, was used as the anolyte. The catholyte consisted of water, terephthalic acid, ammonia and a soluble ammonium salt, ammonium carbonate ($(NH_4)_2CO_3$). The cathode was lead. Results are in Table I. Comparative data from German Offen. No. 2,642,496 are included. Current efficiency (C.E.) of '496 is calculated.

TABLE I

Electrochemical Reduction of
Terephthalic Acid - $(NH_4)_2CO_3$ Electrolyte
LEAD CATHODE

| Run No. (5302) | 24[a] | 28[a] | 26[b] | Comparative Run[c] |
|---|---|---|---|---|
| Conditions | | | | |
| $(NH_4)_2CO_3$ - g/l | 15 | 15 | 15 | 13.6 |
| Ammonia - g/l | * | * | * | 16 |
| Terephthalic Acid (TA) - g/l | 50 | 50 | 50 | 42.3 |
| Current Density - A/dm$^2$ | 6.5 | 6.5 | 6.5 | 10 |
| Faradays/mole TA | 3.7 | 3.7 | 3.7 | 15.3 |
| Actual Run Time - Minutes | 120 | 120 | 120 | 300 |
| Results | | | | |
| TA Conversion | 36 | 35 | 18 | 100 |
| pHMBA-Yield | 25 | 27 | 8 | 91 |
| Current Efficiency | 27 | 29 | 9 | (26)[c] |
| Catholyte Analysis** - End of Run - mg/ml | | | | |
| pHMBA | 10.2 | 11.2 | 3.58 | N.R. |
| Terephthalic Acid (TA) | 28.2 | 29.8 | 37.9 | N.R. |
| 4-CBA | 0.54 | 0.18 | 0.56 | N.R. |

Notes:
N.R. — Not reported.
*Ammonia was added until terephthalic acid dissolved.
**Analysis of product by liquid chromatography.
[a]Continuous operation with no interruption. Cells were not shorted.
[b]Interrupted operation - 15 minutes on, 1 minute off until 120 minutes. Cell was not shorted out.
[c]Data from Germ. Offen. 2,642,496. Current efficiency (C.E.) is calculated. Cell was shorted out for 1 minute each hour.

Runs No. (5302) 24[a] and 28[a] duplicate run conditions of Comparative Run (c) based on calculated current efficiency, except that the runs were not interrupted and the cells were not shorted. It is presumed that application of 15.3 Faradays per mole of terephthalic acid in Runs No. (5302) 24[a] and 28[a] would have resulted in 100% terephthalic acid conversion. Run (5302) 26[b] using interrupted operation resulted in lower conversion of terephthalic acid than Runs No. (5302) 24 and 28, indicating that interrupted operation did not improve current efficiency under these conditions.

EXAMPLE II

The procedure of Example I was repeated using ammonium chloride and ammonium sulfate as the ammonium salts. The results are in Table II.

TABLE II

Electrochemical Reduction of
Terephthalic acid - $NH_4Cl$ - $(NH_4)_2SO_4$ Electrolytes
Lead Cathode

| Run No. (5302) | 8 | 20 | 25 |
|---|---|---|---|
| Conditions | | | |
| $NH_4Cl$ - g/l | 10 | 10 | |
| $(NH_4)_2SO_4$ - g/l | | | 15 |
| Ammonia - g/l | 14 | * | * |
| Terephthalic Acid (TA) - g/l | 50 | 100 | 50 |
| Current Density - (C.D.) A/dm$^2$ | 6.5 | 6.5 | 6.5 |
| Faradays/mole TA | 3.7 | 3.7 | 3.7 |
| Actual Run Time - Minutes | 120 | 240 | 120 |
| Results | | | |
| TA Conversion | 72 | 83 | 51 |
| pHMBA-Yield | 60 | 56 | 31 |
| C.E. | 64 | 60 | 32 |
| Catholyte Analysis** - End of Run - | | | |
| pHMBA, mg/ml | 26.7 | 47.4 | 13.9 |
| Terephthalic Acid (TA), mg/ml | 13.9 | 15.9 | 24.0 |
| 4-CBA, mg/ml | 0.29 | 0.73 | 0.35 |

*Ammonia was added until terephthalic acid dissolved. Measured pH was less basic than Run 8.
**Analysis by liquid chromatography.

Comparison of the data in Tables I and II indicates that ammonium chloride is a more suitable electrolyte salt with a lead cathode than either ammonium carbonate or ammonium sulfate. The chloride ion is at least twice as effective as the carbonate or sulfate ions.

EXAMPLE III

The procedure of Example I was repeated using ammonium chloride and ammonium sulfate as the ammonium salts and mercury as the cathode. The liquid mercury was placed in the bottom of the glass beaker which functioned as the cell holder. Electrical contact was made with the liquid mercury by means of a suitable conductor. Results are in Table III.

TABLE III

Electrochemical Reduction of Terephthalic Acid -
Mercury Cathode

| Run No. (5302) | 144 | 162 | 136 | |
|---|---|---|---|---|
| Conditions | | | | |
| Salt | $NH_4Cl$ | $(NH_4)_2SO_4$ | $NH_4Cl$ | |
| g/l | 20 | 40 | 20 | |
| Ammonia g/l | 26 | 32 | 24 | |
| Terephthalic Acid (TA) g/l | 123 | 197 | 117 | |
| C.D. - A/dm$^2$ | 12 | 12 | 12 | |
| Faradays/Mole of TA | 3.7 | 3.7 | 3.7 | 5.6 |
| Time - Minutes | 120 | 120 | 120 | 180 |
| Results - % | | | | |
| TA Conversion | 97 | 96 | 97 | 98 |
| pHMBA Yield | 85 | 93 | 89 | 74 |
| C.E. | 91 | 99 | 96 | 53 |
| Catholyte Analysis** - End of Run - mg/ml | | | | |
| pHMBA | 96.5 | 167.3 | 92.8 | 77.1 |
| Terephthalic Acid (TA) | 3.22 | 8.2 | 3.32 | 2.72 |
| 4-CBA | 0.48 | 1.2 | 0.34 | 0.07 |
| Toluic Acid | 0.67 | 0.9 | 0.74 | 6.45 |
| p-Xylenediol | N.D. | N.D. | N.D. | 13.6 |

Note:
N.D. — Not detected by liquid chromatography.
**Analysis by liquid chromatography.

The above data indicate the improvement in terephthalic acid conversion and increased yield of pHMBA obtained with mercury cathode at high current efficiency versus results obtained with lead cathode in Examples I and II. The data indicate ammonium salts of sulfate or chloride are equally suitable with mercury cathode whereas ammonium chloride is preferable with lead cathode as shown in Table II of Example II. Toluic acid also resulted as product in Runs No. (5302) 144, 162 and 136 in Table III. Continuation of Run No. (5302) 136 to 180 minutes resulted in a rapid increase in production of toluic acid and production of p-xylenediol. Current efficiency dropped. pHMBA was converted to other products (toluic acid and p-xylenediol).

EXAMPLE IV

The procedure of Example I was repeated using a lead amalgam cathode. The lead amalgam was prepared by abraiding the surface of electrolytically pure lead to remove any metal oxidation and then contacting the abraided metal surface with mercury to form the amalgam. Mercury of 99.9% purity was used as the bath for the abraided solid lead cathode. The lead amalgam of mercury formed in the surface of the lead at room temperature. Results are in Table IV.

TABLE IV

Electrochemical Reduction of Terephthalic Acid - Lead Amalgam Cathode

| Run No. | (5302) 196 | (5593) 100 | (5593) 102 |
|---|---|---|---|
| Conditions | | | |
| Salt | $(NH_4)_2SO_4$ | $(NH_4)_2SO_4$ | $(NH_4)_2SO_4$ |
| g/l | 40 | 40 | 40 |
| Ammonia - g/l | 23 | 21 | 30 |
| Terephthalic Acid (TA) | | | |
| g/l | 107 | 106 | 169 |
| C.D. - $A/dm^2$ | 13.5 | 13.5 | 13.5 |
| Faradays/Mole of TA | 3.7 | 3.7 | 3.7 |
| Time - Minutes | 120 | 120 | 240 |
| Results - % | | | |
| TA Conversion | 92 | 87 | 88 |
| pHMBA | | | |
| Yield | 93 | 84 | 83 |
| C.E. | 99 | 91 | 89 |
| Catholyte Analysis** - End of Run - mg/ml | | | |
| pHMBA | 91.7 | 82.4 | 128.2 |
| Terephthalic Acid (TA) | 8.9 | 13.5 | 19.9 |
| 4-CBA | 1.0 | 1.9 | 0.7 |
| Toluic Acid | N.D. | N.D. | N.D. |

Note:
N.D. — Not detected by liquid chromatography.
**Analysis by liquid chromatography.

The above data indicate the high conversion of terephthalic acid to p-hydroxymethylbenzoic acid (pHMBA) and improved current efficiency with lead amalgam cathode versus lead cathode. Current efficiency improved over use of a lead cathode as indicated in Tables I and II. Less toluic acid resulted than with use of a mercury cathode as shown in Table III.

EXAMPLE V

Two continuous reductions of terephthalic acid to p-hydroxymethylbenzoic acid were carried out in an electrolysis cell in the following manner to compare the current efficiency obtained with a lead cathode and with a lead amalgam cathode in continuous operation. One cathode was electrically pure lead. The other cathode was electrically pure lead amalgamated with 99.9% pure mercury. In construction the two compartment electrolysis cell comprised an inlet plate of polyvinylchloride (PVC) which was fitted to a second plate of the same size of lead amalgam which constituted the cathode. PVC inserts between the cathode plate and the semipermeable membrane acted as spacers to separate the cathode and membrane sufficiently to permit catholyte flow. The anode was an electrically pure ½-inch titanium plate coated with platinum to a thickness of 250 micro-inches. Anode and membrane were separated by PVC spacers to permit the anolyte to flow through the cell. An external reservoir for the anolyte served as an oxygen gas separator. An external reservoir for the catholyte served as a hydrogen gas separator. In operation, electrolyte was continuously pumped from the reservoir to the electrolysis cell and returned to the reservoir through a heat exchanger. No addition of a mercury salt was made to either catholyte. Details are in Table V.

TABLE V

Reduction of pHMBA
Current Efficiency - Continuous Operation
Lead and Lead Amalgam Cathodes

| | Run No. 5268-164 | Run No. 5593-140 |
|---|---|---|
| Conditions | | |
| Cathode | Lead | Lead Amalgam |
| Salt | $NH_4Cl$ | $(NH_4)_2SO_4$ |
| g/l | 10 | 30–44 |
| pH | 7.0–9.0 | 8.4–9.1 |
| TA - g/l | 20–100 | 40–120 |
| Current Density $A/dm^2$ | 6.5–13 | 50 |
| Results | | |
| pHMBA - % Current Efficiency | | |
| 0–2 Hours of Run | 57 | 86 |
| 2–4 Hours of Run | 21 | 71 |
| 4–6 Hours of Run | 4 | 41 |

Ammonium chloride ($NH_4Cl$) was used as the electrolyte with the lead cathode on the basis of data in Example II indicating $NH_4Cl$ gave higher terephthalic acid (TA) conversion to pHMBA and higher current efficiency than did ammonium sulfate $(NH_4)_2SO_4$ as an electrolyte.

Data in Table V indicate that even though a more efficient electrolyte was used with the lead cathode, better results were obtained with the lead amalgam cathode with an electrolyte which gave poor results with the lead cathode. However, with continuous operation, current efficiency declined to inefficient levels with both cathodes and both electrolytes.

EXAMPLE VI

Amalgam analyses were made before and after a continuous reduction to determine if loss of mercury from the lead amalgam surface of the cathode occurred in an electrochemical reduction of terephthalic acid. Accordingly, energy dispersion analyses of X-rays (EDAX) to obtain qualitative and quantitative analysis of the amalgam cathode surface were made before and after the run 5593-140 reported in Example V. Mercury content on the lead amalgam surface of the cathode had decreased after the run. Lead and iron content on the cathode surface had increased. After the run, the surface was lightly abraided to expose a fresh surface and the surface was again analyzed by EDAX. Results are in Table VI.

TABLE VI

EDAX Analysis of Lead Amalgam Cathode Surfaces

| | Element, % | | |
|---|---|---|---|
| | Hg | Pb | Fe |
| Freshly Amalgamated | 74 | 26 | — |

TABLE VI-continued

EDAX Analysis of Lead Amalgam Cathode Surfaces

| | Element, % | | |
|---|---|---|---|
| | Hg | Pb | Fe |
| After Run - No Hg Added | | | |
| Top Layer Surface | 22 | 77 | 0.6 |
| Fresh Surface | 32 | 67 | 0.3 |

The above data indicate that electrochemical reduction of terephthalic acid reduces the mercury surface content of an amalgamated lead cathode and lead content increases.

EXAMPLE VII

The lead amalgam cathode used in Examples V and VI was re-amalgamated in the procedure of Example IV. The procedure of Example V was repeated without any addition of mercury. The electrolyte was analyzed three times by atomic absorption (AA) of mercury using standard analytical techniques, twice before the 5-hour run and once after the 5-hour run. The first analysis was of the freshly prepared catholyte. The second analysis was after pumping the catholyte through the cell so as to contact the lead amalgam cathode. Mercury content of the catholyte was increased by contact with the lead amalgam cathode and, as indicated by the third analysis, decreased with subsequent reduction of terephthalic acid. Details are in Table VII.

TABLE VII

Loss of Mercury From Catholyte During Reduction

Run 5995-1

| Conditions | | |
|---|---|---|
| Cathode | Lead Amalgam | |
| Electrolyte | | |
| $(NH_4)_2SO_4$, g/l | 46 | |
| Ammonia, g/l | 12 | |
| pH - Start/End | 8.2/9.0 | |
| Current Density, $A/dm^2$ | 54 | |
| TA, g/l | 48–130 | |
| Results | | |
| C.E. % pHMBA - During 5 Hr Run | 90 ± 3 | |
| $H_2$ Prod. - $ft.^3$ - Total over 5 Hrs | 1.2 | |
| Analyses of Catholyte | Hg | Pb |
| Freshly Prepared Catholyte | 10 ppb | 0.2 ppm |
| Catholyte After Pumping Through Cell over Cathode for 10 minutes, No current applied | 625 ppb | 10 ppm |
| Catholyte After 5 Hr Reduction of TA | 400 ppb | 5 ppm |

Note:
ppb — parts per billion.
ppm — parts per million.

EXAMPLE VIII

In the procedure of Example V two continuous reductions of terephthalic acid were carried out in an electrolysis cell to compare current efficiency obtained with and without the addition of a mercury salt. The cathode was electrically pure lead amalgamated with 99.9% mercury. Periodic additions of mercuric acetate $(Hg(Ac)_2)$ were made each hour to the electrolysis cell during the course of the run. A control run was also made wherein mercuric acetate was not added to the electrolysis cell. The results of continuous operation using ammonium sulfate as the required salt are in Table VIII.

TABLE VIII

Reduction of Terephthalic Acid to pHMBA In Presence of Hg In Catholyte
Runs 5995

| | Time - Hrs | | | | |
|---|---|---|---|---|---|
| | 13 (No Hg Added) | | 22(a) (With Addition of Hg) | | |
| After | $H_2/\frac{1}{2}$ Hr. Prod. ($ft^3$) | C.E./Hr % | Accum. Hg ppm | $H_2/\frac{1}{2}$ Hr. Prod. ($ft^3$) | C.E./Hr % |
| 1 Hr | 0.12 | 91.4 | — | 0.15 | 90.3 |
| 2 hrs | 0.26 | 81.0 | 9.2 | 0.29 | 72.5 |
| 2.5 hrs | 0.34 | — | 27.0 | 0.40 | — |
| 3 hrs | 0.41 | 68.4 | 88.0 | 0.50 | 61.6 |
| 3.5 hrs | 0.48 | — | 257.4 | 0.43 | — |
| 4 hrs | 0.56 | 44.3 | — | 0.16 | 57.5 |
| 5 hrs | — | — | — | 0.14 | 97.3 |

(a)Analysis of catholyte after Run 5995-22 by atomic absorption (AA) indicated 7.9 parts per billion of Hg and 12.2 parts per million of Pb indicating Hg had plated out on the Pb cathode.

The data indicate that as the addition of mercury began to build beyond 80 parts per million(ppm), the amount of hydrogen evolved began to decrease and the current efficiency (C—E.) began to increase. The above data indicate that the presence of over 100 ppm of mercury reversed the trend in current efficiency percent from a negative to a positive rate under the conditions of Example V.

EXAMPLE IX

The procedure of Example V was repeated in multiple runs using mercuric acetate additions in all runs. The same cathode used in Example VIII was used in Example IX without cleaning and/or amalgamation with a mercury bath. The results of continuous operation using ammonium sulfate and one run with ammonium carbonate as the required salt and with addition of mercuric acetate over a period of days are in Table IX.

TABLE IX

Electrochemical Reduction of TA to pHMBA With Mercuric Acetate

| Run No. (5995) | Run Hrs. Each Day | C.D. | Hg Added ppm | F.C. | pHMBA g/hr | pHMBA % C.E. |
|---|---|---|---|---|---|---|
| 51-7/11 | 4.5 | 54 | 385 | 0.098 | 123 | 74 |
| 51–18 | 5.0 | 54 | 332 | 0.148 | 123 | 73 |
| 63 | 5.0 | 54 | 173 | 0.179 | 111 | 66 |
| 66 | 6.0 | 54 | 76 | 0.108 | 148 | 86 |
| 66 | 5.5 | 54 | 243 | 0.174 | 145 | 87 |
| 68 | 5.5 | 68 | 294 | 0.116 | 176 | 84 |
| 70 | 4.5 | 81 | 155 | 0.112 | 196 | 84 |
| 73 | 5.5 | 88 | 303 | 0.144 | 203 | 79 |
| 74 | 6.0 | 88 | 305 | 0.152 | — | — |
| 78 | 7.0 | 88 | 603 | 0.164 | 211 | 82 |
| 79 | 6.5 | 88 | 454 | 0.189 | 214 | 79 |
| 85 | 7.0 | 88 | 452 | 0.193 | 219 | 81 |
| 86 | 7.0 | 88 | 454 | 0.193 | 212 | 78 |
| 110* | 13.5 | 75 | 733 | 0.180 | 148 | 72 |
| Total Hrs** | 88.5 | | | | | |

Notes:
C.D. = Current Density $A/dm^2$ at end of each run
F.C. = Final Concentration of pHMBA in g/ml
C.E. = Current Efficiency
*Used $(NH_4)_2CO_3$. All others used $(NH_4)_2SO_4$. Same cell was used in all runs with no current reversals or shorting.
**Total accumulative hours on same cathode without cleaning and/or amalgamation with a mercury bath.

The data indicate the percent current efficiency (C.E.) and production of p-hydroxymethylbenzoic acid remained at high levels under conditions of continuous operation.

As indicated in Table IX, total accumulated 88.5 hours were made on the same cathode without need for procedures other than described to overcome cathode deactivation. The same cathode had previously been used for 5.5 hours in Example VIII, Table VIII, Run No. (5995) 22, for total accumulated 94 hours without need for cleaning of the cathode amalgam surface and/or amalgamation with a mercury bath.

What is claimed is:

1. A process for the preparation of p-hydroxymethylbenzoic acid which comprises electrochemical reduction of terephthalic acid in an electrolysis cell wherein (a) the cathode is solid and metal, said solid, metal cathode having an overlay surface of an amalgam of mercury, said metal of said cathode having a hydrogen overvoltage which is greater than the potential for the reduction of terephthalic acid to p-hydroxymethylbenzoic acid, and (b) sufficient mercury is added therein as a mercury compound to maintain said process.

2. The process of claim 1 wherein the catholyte of said process comprises a solvent, terephthalic acid, ammonia, an ammonium salt and a mercury compound, (b) the temperature of said catholyte is within the range of from about 0° C. to about 100° C., and (c) current density applied to said process is within the range of from about 1 to 200 A/dm$^2$.

3. The process of claim 1 wherein said metal of said cathode is selected from the group consisting of lead, and alloys of lead with metals selected from the group consisting of cadmium, antimony, tin and bismuth.

4. The process of claim 3 wherein said metal of said cathode is lead and surface of said cathode is lead amalgam.

5. The process of claim 2 wherein said solvent is water.

6. The process of claim 2 wherein said mercury compound is a soluble salt of mercury.

7. The process of claim 6 wherein said soluble salt of mercury is selected from the group consisting of mercuric acetate, mercuric bromide, mercuric chlorate, mercuric chloride, and mercuric cyanide.

8. The process of claim 7 wherein said soluble salt of mercury is mercuric acetate.

9. The process of claim 2 wherein said ammonium salt of said catholyte is selected from the group consisting of ammonium chloride, ammonium sulfate and ammonium carbonate.

10. The process of claim 2 wherein concentration of said terephthalic acid is greater than 2 percent by weight of the total solution.

11. The process of claim 2 wherein concentration of said ammonium salt is within the range of from about 0.1 to about 10% by weight of the total solution.

12. The process of claim 11 wherein concentration of said ammonium salt is within the range of from about 0.1 to about 1.0% by weight of the total solution.

13. The process of claim 2 wherein concentration of said ammonia as ammonium hydroxide is within the range of from about 1 gram of ammonium hydroxide per 2 grams of terephthalic acid to about 1 gram of ammonium hydroxide per gram of terephthalic acid and wherein the pH of the resulting solution is at least 6.5.

14. The process of claim 13 wherein said pH of resulting solution is within the range of from about 8.5 to about 9.5.

15. The process of claim 2 wherein said current density is within the range of from about 20 to about 100 A/dm$^2$.

16. The process of claim 1 wherein terephthalic acid reduction to p-hydroxymethylbenzoic acid is less than 100%.

17. The process of claim 16 wherein said terephthalic acid reduction to p-hydroxymethylbenzoic acid is less than 96%.

18. The process of claim 2 wherein said p-hydroxymethylbenzoic acid is isolated from said catholyte by acidification of said catholyte, filtration of said catholyte at a temperature within the range of from about 75° C. to about 100° C. to remove terephthalic acid, and cooling the mother liquor at a temperature below 40° C.

19. The process of claim 1 wherein said process uses a separating diaphragm.

20. The process of claim 19 wherein said separating diaphragm is of the homogeneous type.

21. The process of claim 20 wherein said diaphragm is a membrane of perfluorosulfonic acid.

22. The process of claim 1 wherein said process is a continuous process.

23. A process for the preparation of p-hydroxymethylbenzoic acid which comprises electrochemical reduction of terephthalic acid in an electrolysis cell wherein (a) the cathode is solid and metal, said solid, metal cathode having an overlay surface of an amalgam of mercury, said metal of said cathode having a hydrogen overvoltage which is greater than the potential for the reduction of terephthalic acid to p-hydroxymethylbenzoic acid, (b) sufficient mercury is added therein as a mercury compound to maintain said process, (c) said process is a continuous process; (d) the catholyte of said process comprises water, terephthalic acid, ammonia, mercuric acetate, an ammonium salt selected from the group consisting of ammonium chloride, ammonium sulfate and ammonium carbonate, the temperature of said catholyte is within the range of from about 0° C. to 100° C.; (e) current density applied to said process is within the range of from about 1 to 200 A/dm$^2$; (f) concentration of said terephthalic acid in said catholyte is greater than 2% by weight of the total solution; (g) concentration of said ammonium salt in said catholyte is within the range of from about 0.1 to about 10% by weight of the total solution; (h) concentration of said ammonia as ammonium hydroxide is within the range of from about 1 gram of ammonium hydroxide per 2 grams of terephthalic acid to about 1 gram of ammonium hydroxide per gram of terephthalic acid and wherein pH of the resulting solution is within the range of from about 6.5 to about 9.5; (i) said metal of said cathode is selected from the group consisting of lead and alloys of lead with metals selected from the group consisting of cadmium, antimony, tin and bismuth; (j) said reduction of said terephthalic acid is less than 96%; (k) said process uses a separating diaphragm.

* * * * *